United States Patent [19]

Congleton

[11] Patent Number: 4,552,404
[45] Date of Patent: Nov. 12, 1985

[54] NEUTRAL BODY POSTURE CHAIR

[76] Inventor: Jerome J. Congleton, 2728 San Felipe, College Station, Tex. 77840

[21] Appl. No.: 541,093

[22] Filed: Oct. 12, 1983

[51] Int. Cl.$^4$ ............................................... A47C 1/02
[52] U.S. Cl. ...................................... 297/330; 297/41; 297/445; 297/458; 297/DIG. 10
[58] Field of Search ................. 297/71, 195, 347, 345, 297/330, 458, 459, 445, 423, DIG. 10

[56] References Cited

U.S. PATENT DOCUMENTS

| | | | |
|---|---|---|---|
| 2,458,463 | 1/1949 | Bell | 297/431 |
| 2,970,638 | 2/1961 | Halter | 297/458 X |
| 3,029,106 | 4/1962 | McGuire | 297/347 X |
| 3,503,649 | 3/1970 | Johnson | 297/458 X |
| 3,669,493 | 6/1972 | Vowels | 297/423 X |
| 3,740,096 | 6/1973 | Bridger | 297/459 |
| 3,754,787 | 8/1973 | Garber | 297/345 X |
| 3,863,978 | 2/1975 | Gillings, Jr. | 297/195 |
| 4,083,599 | 4/1978 | Gaffney | 297/347 |
| 4,249,774 | 2/1981 | Andreasson | 297/347 X |
| 4,367,897 | 1/1983 | Cousins | 297/284 |

*Primary Examiner*—James T. McCall
*Attorney, Agent, or Firm*—N. J. Aquilino

[57] ABSTRACT

A neutral body posture chair to support a user in a neutral body posture position defined as the natural position a body assumes in weightlessness where the muscle, tendon, and ligament systems acting over the joints are in total balance wherein the trunk of the body forms an angle of approximately 127 degrees with respect to the upper legs and the upper legs form an angle of approximately 127 degrees with the lower legs. The chair includes a seat formed into a bowl at the pelvic area, leg troughs support the upper legs and raised sides to maintain the user in the selected position. The seat further includes an elevated pommel which supports the pubis bone of the user to maintain the user in the desired neutral body posture angle without sliding out of the seat. The chair assembly includes a back rest, footrests, and a suitable base. The chair includes means for adjusting the vertical height of the seat, the tilt angle of the seat, the angle of the backrest, and vertical height of the backrest.

14 Claims, 17 Drawing Figures

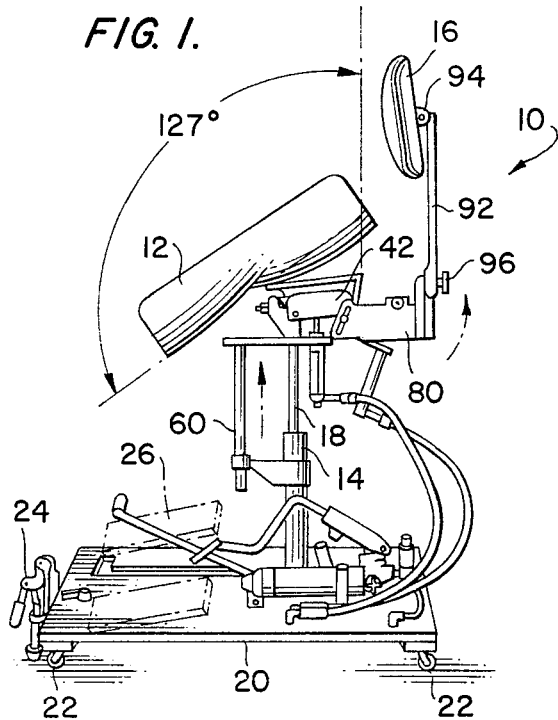
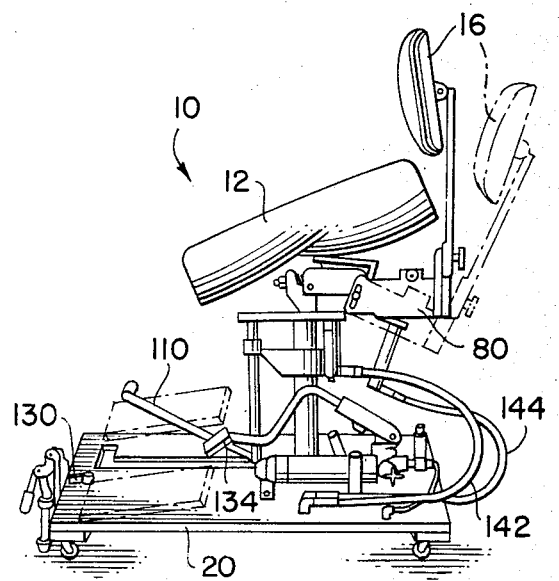
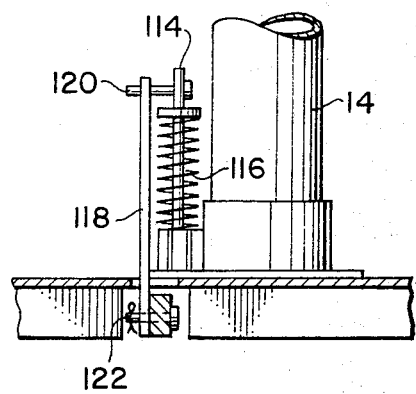
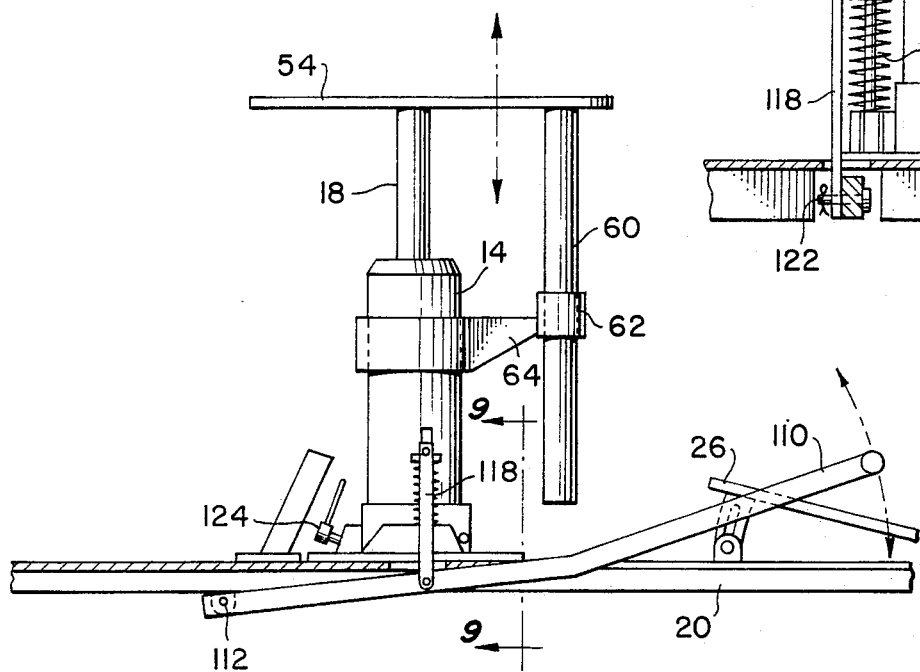

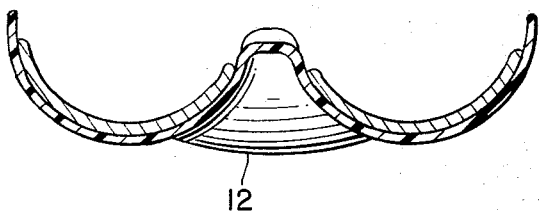
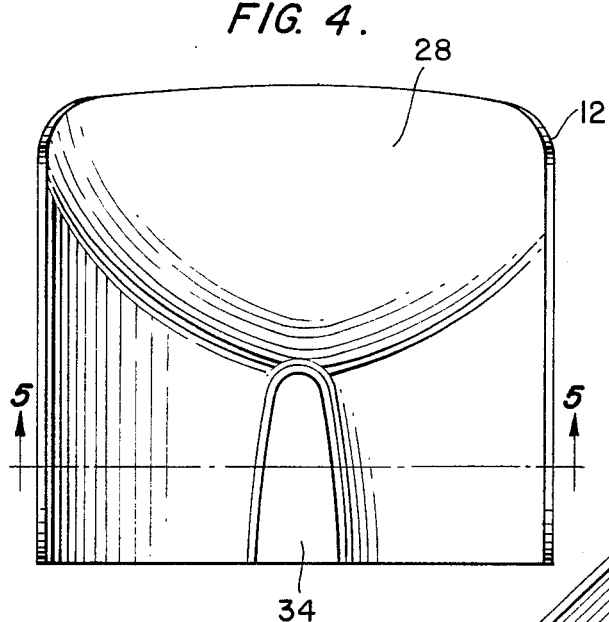
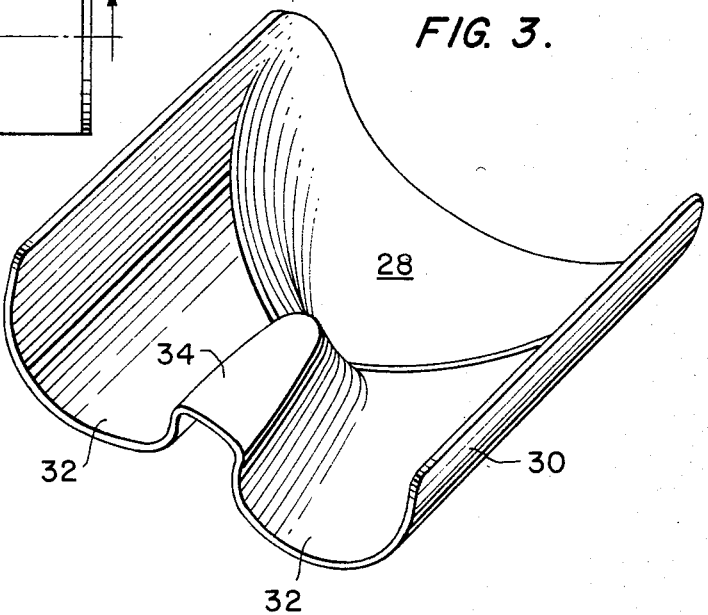
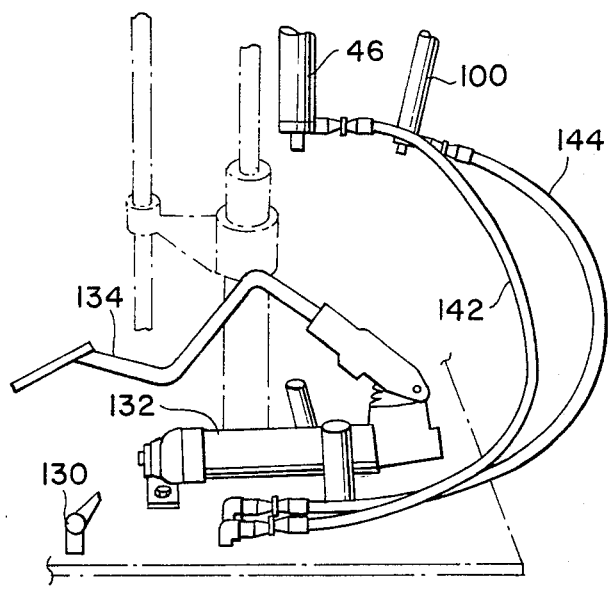
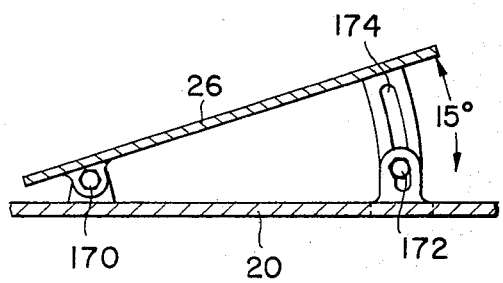

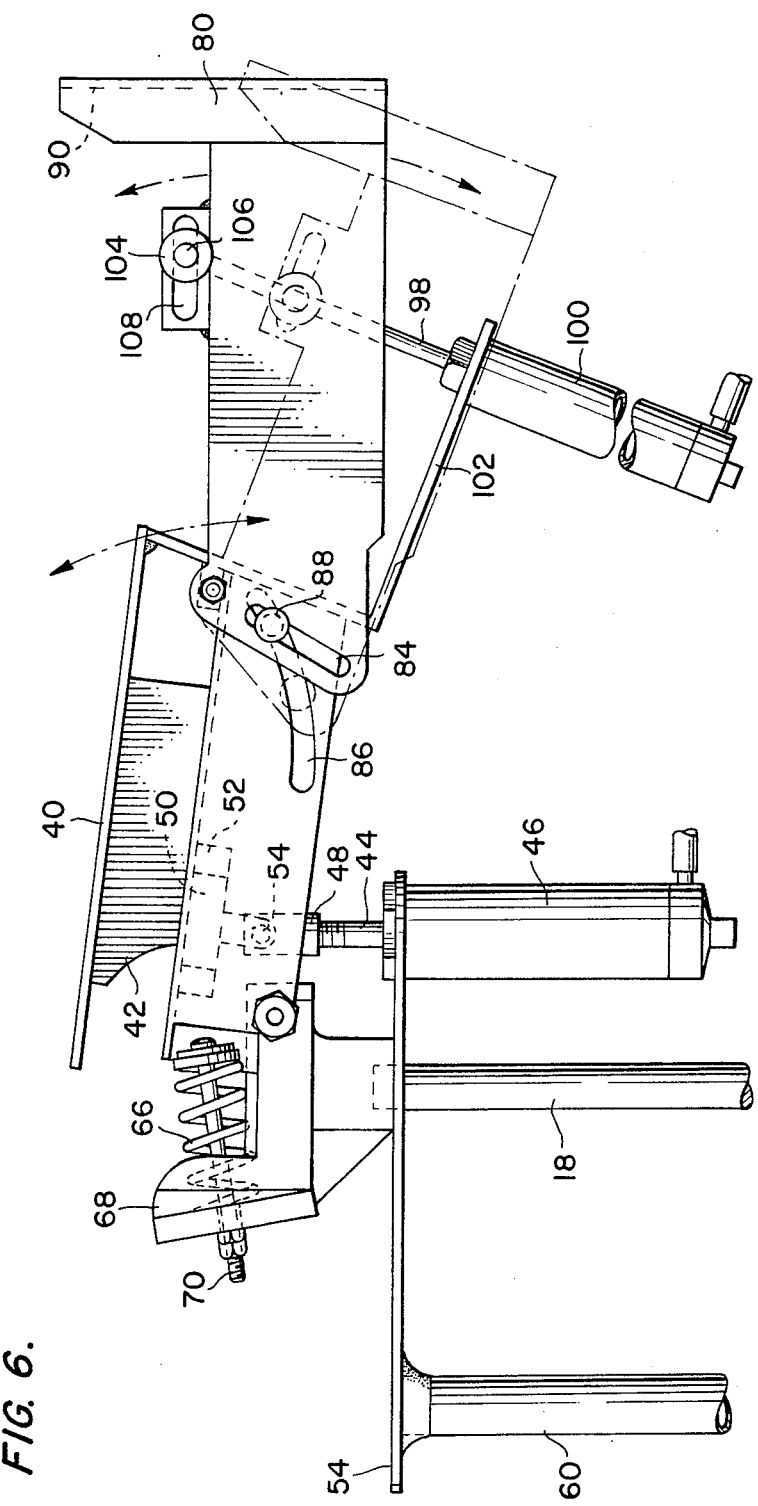
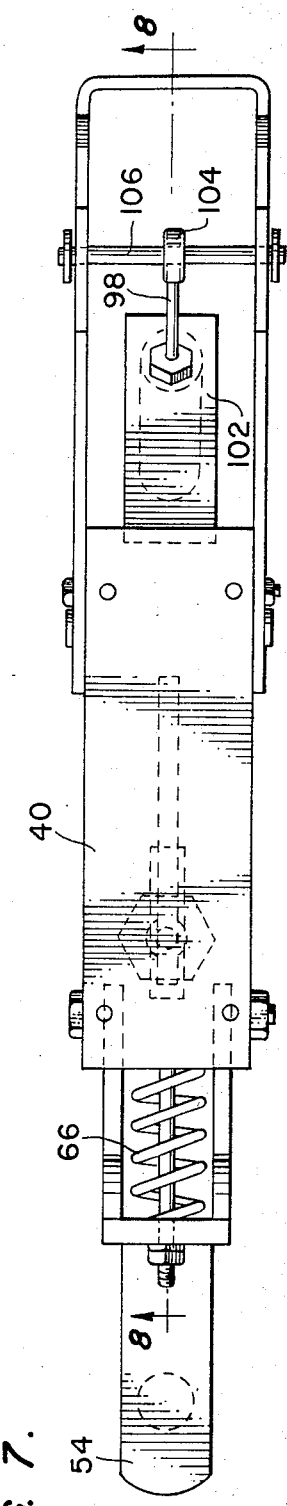
FIG. 6.
FIG. 7.

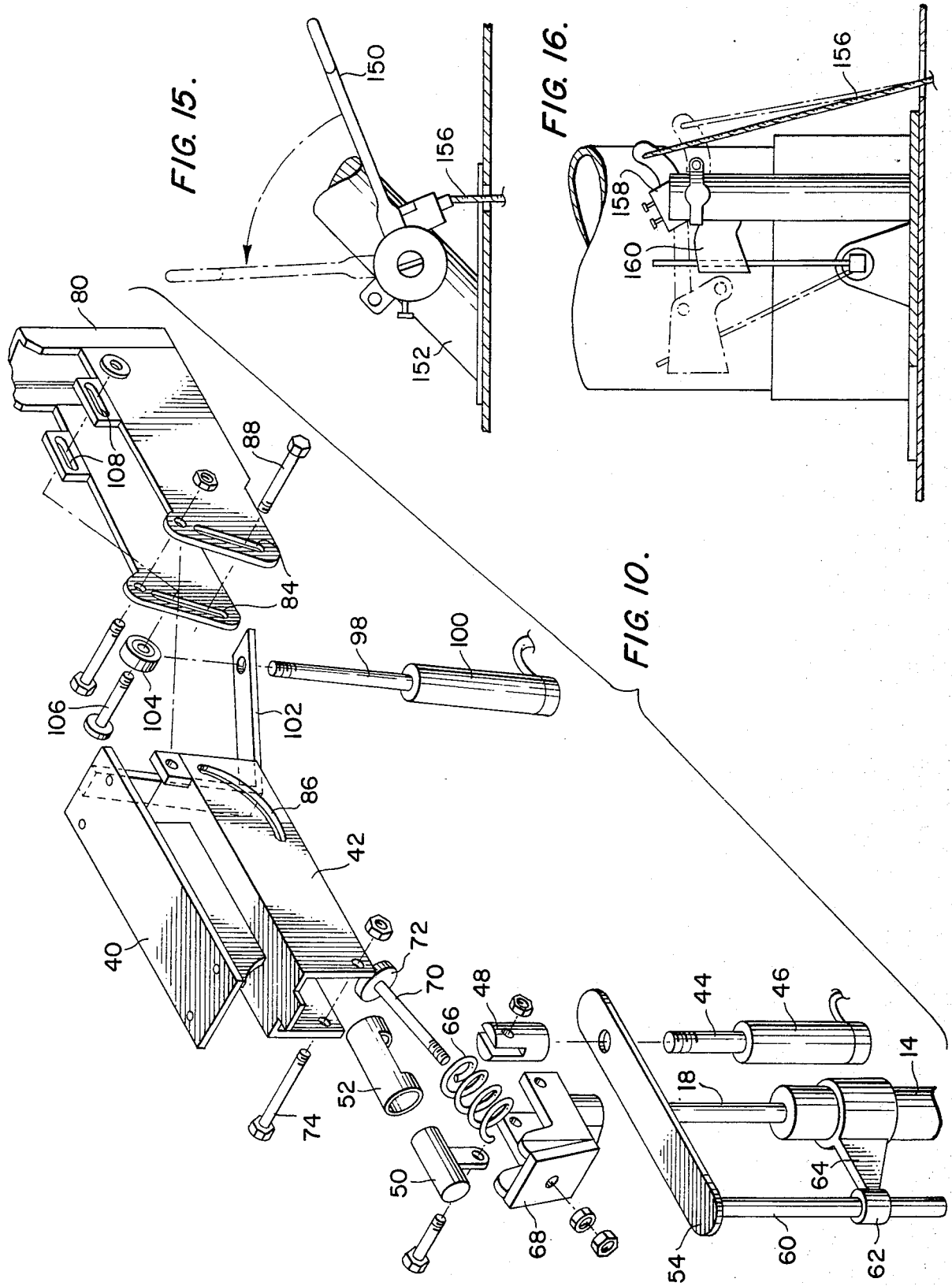

NEUTRAL BODY POSTURE CHAIR

BACKGROUND OF THE INVENTION

One of the most stressful and aggravating problems encountered in the sedentary work force involves the question of proper body support in a seated position. This is particularly true for people suffering back problems since an extremely large percentage of the civilized world's population experience such problem. The present invention relates to a neutral posture chair, and in particular to a neutral posture surgical chair for microsurgeons which reduces or eliminates fatigue experienced by the surgeon due to body posture during microsurgical procedures while the surgeon performs microscopic operations while seated.

Microsurgery is a practice of operative surgery utilizing magnification. The surgeon sits to increase his stability, steadiness, and precision. It is not uncommon for a surgeon to be seated for an extremely long period of time, up to as many as twelve hours fo complicated surgeries such as might be experienced in surgical replantation procedures and the like. Microsurgery presents many special problems regarding visual information, fine manipulation, and tremor control. Among the factors which affect tremor are the body posture, point of limb support, direction of movement, design fo rotatability, and strenous exertion. During extended seated operations, muscular fatigue occurs in the low back, the mid back, the upper back, the shoulders, the neck, the feet, the lower legs, the upper legs, and in the buttocks.

Ergonomics, defined as "the study as man-machine interface", has promoted research in the area o environmental conditions and their effect on work. Many of the findings of the Erogonomics study have been implemented in the industry, particularly in Europe. Ergonomics findings have been applied to the aerospace program in the United States through extensive studies at the National Aeronautics and Space Administration Space Center in Houston on the influence of zero-g and acceleration on the human factors of spacecraft design. However, Ergonomics has all but been ignored in a surgical context because of the intense interest in the practical details of operative procedures. However, the newness and the technical problems of microsurgery have provided a special opportunity to develop the application of Ergonomics to surgery.

In a study by A. C. Mandal, "The Seated Man in 1981", it was indicated that almost half of the industrialized world is thought to be suffering from some form of back complaints. Although industry has made many advances toward eliminating back injury through improved mechanical material handling device systems, cost every year for sick pay, medical treatment, hospitalization, rehabilitation, placement of the physically restricted worker, and disablement compensation and pensions consume enormous sums of money and are exponentially increasing. As industry makes advances in technology, computerization, and material handling, there are concomitant increases in sedentary tasks as the amount of seated time increases. Every day people sit for many hours in many supposedly comfortable and biomechanically designed chairs, such as office chairs, lounge chairs, automobile or airline seats. Notwithstanding the special seat designs, the most common complaints of people with back pain is the inability to sit in comfort, with accompanying difficulty in straightening the back on rising.

Therefore, it is the purpose of this invention to provide and improve neutral posture chair structure which overcomes the disadvantages of the prior art systems and the fundamental misconceptions as to the correct sitting posture. The present invention provides a chair structure which is less fatiguing and more comfortable to sit in based on the neutral body posture position. The conventional correct sitting posture was generally thought to be that the body should be upright with the back straight, where the upper leg forms a 90 degree angle with the trunk; the lower leg forms a 90 degree angle to the upper leg, and the upper arms are hanging vertically at a person's side with the lower arm 90 degrees to the upper arm. However, studies of the type mentioned hereinabove, including those taken in weightlessness and under water conditions have found that the body assumes a neutral posture position where the upper leg forms of an angle with respect to the trunk of approximately 127 degrees and the lower leg forms approximately the same angle with respect to the upper leg. This angle varies slightly due to the physical structure of particular individuals and may vary somewhere between 105 and 135 degrees. It has also been found that a more upright posture for performing sedentary tasks is better for breathing and swelling of the ankles is reduced, legs are able to move more freely, and rising from the seat is easier because the posture is a compromise between standing and sitting. Further studies have also found that a good chair structure should permit changing of the posture which facilitates blood flow and venous return which will help prevent fatigue. An important component of a chair is a well designed back rest which permits support of the lumbar spine yet does not interfere with desired movement of the shoulders and the arms. Levels of disk pressure and electromyography fall when the back of a seated subject is supported. When a chair includes foot controls, back rests provide resistance to force utililize in operating these controls. In particular, foot controls for microsurgery supports allow manipulation of the various controls necessary for the microsurgery thereby eliminating the need of the gloved hands of the surgeon to touch controls allowing them to remain sterile for the duration of the operation.

Electromyogram is the electrical signal associated with the contraction of a muscle. When the body assumes a more neutral posture position, the electromyogram signals decrease indicating a reduction in muscle contraction which results in less fatigue and increases the ability of the seated person to remain in the optimum position for longer periods of time.

Microsurgical chairs which form the present state of the art generally consist of a base structure having three, four or five legs, a flat seat, and some type of adjustable back rest, although a number of microsurgical stool designs eliminate the back rest because microsurgeons tend to sit on the front edge of the seat tilted over the operating table with the abdomen supported so as to be in a leaning over position with the lower arms supported by the operating table, the patient, or mechanical supports specifically designed for that purpose. In studies, it has been found that the surgeon's posture while performing microsurgery tends to not conform to the structural features of the chair, but rather the surgeon assumes more of a sit-stand posture and sits on the front edge of the seat pan primarily because the diameter of the seat pan allows only minor trunk/thigh angle variation. In this position, the surgeon very seldom utilizes a back rest if it is provided and the abdomen is placed against the table or the table extensions. The surgeon places the elbows on the table, table extensions, or does not utilize support in this area. The wrists are usually placed on the patient or on wrist rests. It has been found that the surgeon utilizes all available foot room area and very frequently changes the positions of the lower legs and feet during the course of an operation. The seated posture recommended by Mandal and the NASA studies, among others, appears to closely approximate the seated position of the microsurgeons observed.

In order to overcome the shortcomings of the prior art surgical chairs, as well as chairs in general, the present invention was developed. The present invention is an adjustable chair adapted to support a user in a neutral body posture position, that is the position that the body assumes during weightlessness wherein the muscle, tendon and ligament systems acting on the joints are in total balance and the trunk of the body forms an angle of approximately 127 degrees with respect to the upper legs and the upper legs form a similar angle with respect to the lower legs. With this invention, the user is supported in a posture normally assumed by the body in weightlessness while acting in a normal lg gravity environment. This enables microsurgeons and others in similar sedentary environments to maintain the most natural position the body can assume thereby eliminating the major causes of stress and strain which result from other body positions.

Various factors were considered in the development of the invention, including stability and mobility of the chair. The controls frequently utilized to adjust the height and the tilt of the seat pan as well as the horizontal adjustment of the backrest are foot operated allowing the gloved hands of the surgeon to remain sterile during the operation. The backrest is adjustable both vertically and horizontally and the seat pan height is adjustable to accommodate the various anthropometric differences in the users of the chair and the variable postures they may want to attain. The seat pan tilt is also adjustable so that a trunk/thigh angle of between 90 and 140 degrees is obtainable thereby permitting a change of posture to promote blood distribution and allow for individual variability for the best trunk/thigh angle. The seat pan design also provides a counter ejection force by incorporating a saddle design and further provides additional surface area and support for the thighs by an extension of the seat pan forming leg troughs. Various other features common to microsurgical chairs are included in the present design, including foot rests, conductive casters, sterile construction and material, and so forth.

More specifically, the neutral posture surgical chair of the present invention employs a molded saddle type seat having leg troughs which extend downwardly to support the thighs of the user and a seat pan supporting the pelvic area which includes a central elevated pommel to support the user in the seat when it is tilted. The seat portion is adjustably positioned on a vertical support structure and includes hydraulically operated foot controls which enable the seat to be raised and lowered and tilted to various angles between 90 and 140 degrees with respect to the vertical, preferably at an angle of approximately 127 degrees. The seat structure includes a hydraulically adjustable back support as well as foot rests which are supported on the base of the chair and which are adjustable between an angle of 0 to 15 degrees to accommodate the feet of the user.

Among the objects of the present invention are the provision of a chair adapted to support a user in the neutral body posture position a body would assume in a weightlessness condition, the provision of a chair adapted to position the body of a user in the neutral body position to enable the user to sit in the chair for extensive periods of time in a most comfortable manner without experiencing stress and fatigue normally associated with sedentary positions. A further object of the present invention is to provide a neutral body posture chair specifically designed for use in microsurgery to enable the surgeon to perform tedious operations without attendant inefficiency caused by stress and fatigue.

BRIEF DESCRIPTION OF THE DRAWINGS

FIG. 1 is an elevational view of the chair of the present invention in the raised position.

FIG. 2 is a view of the chair of FIG. 1 in a lowered position.

FIG. 3 is a perspective view of a seat used with the invention of FIG. 1.

FIG. 4 is a top plan view of FIG. 3.

FIG. 5 is an elevational view in section of FIG. 3.

FIG. 6 is an elevational view of a detail of the operating mechanism of FIG. 1.

FIG. 7 is a top plan view of FIG. 6.

FIG. 10 is an exploded view of the detail shown in FIG. 6.

FIG. 11 is an elevational view of a detail of the invention of FIG. 1.

FIG. 12 is another elevational view of a detail of the invention of FIG. 1.

FIG. 13 is a perspective view of still another detail of the invention of FIG. 1.

FIG. 15 is an elevational view of a detail of the invention of FIG. 1.

FIG. 16 is yet another elevational view of a detail of the invention of FIG. 1.

FIG. 17 is still another elevational view partly in section of a detail of the invention of FIG. 1.

DESCRIPTION OF THE PREFERRED EMBODIMENTS

Figure 8:
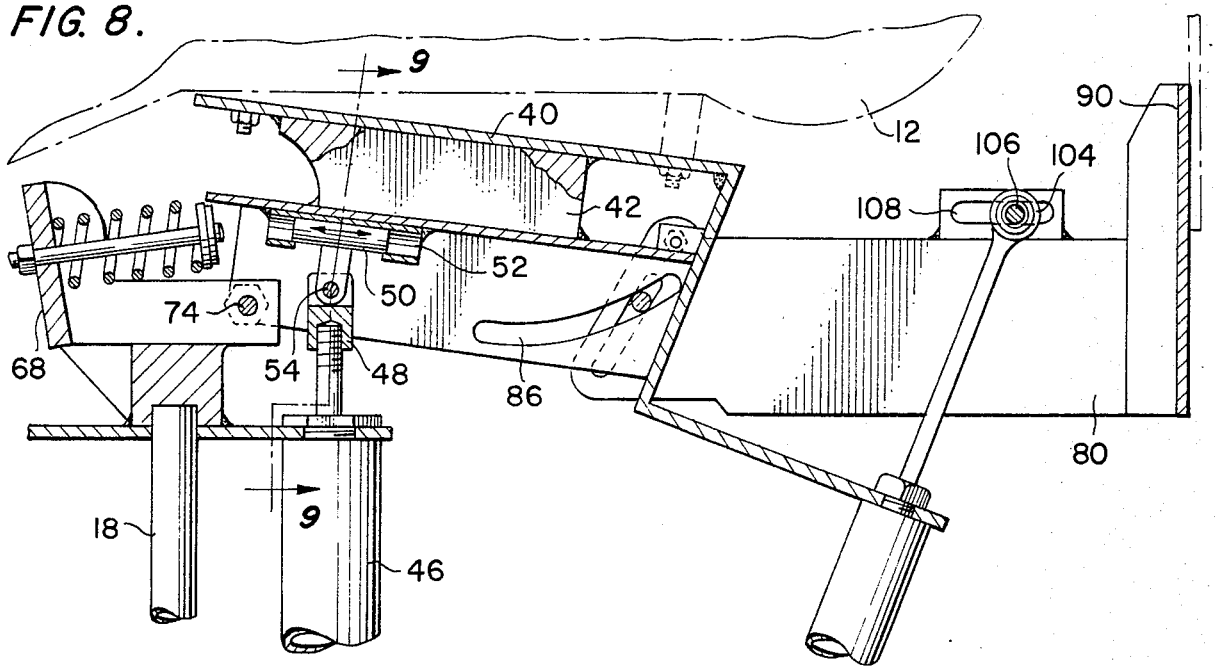
FIG. 8 is a partial sectional view of the detail shown in FIG. 6.
Figure 9:
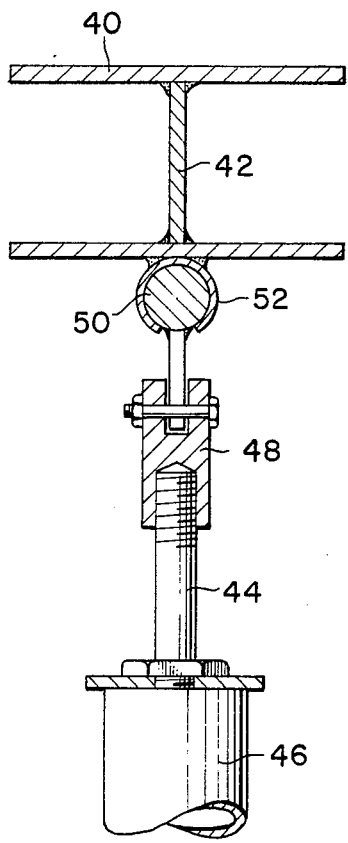
FIG. 9 is a view taken along the lines 9—9 of FIG. 8.

The neutral body posture chair of the present invention is shown in the accompanying drawings wherein like parts are designated by the same numerals.

The chair of the present invention supports a user in the same posture that a body would assume during 0 gravity or weightlessness conditions where the various muscle, tendon and ligament systems which act upon the bones and joints are in total balance. This position has been found to create an angle of approximately 127 degrees between the torso and the upper legs and approximately the same angle between the upper legs and the lower legs. The feet also form an angle of approximately 111 degrees with respect to the lower legs. In this position, the body exhibits the least amount of stresses and strains on its various component parts so that fatigue in this position is greatly reduced.

Because of the greater than 90 degree angles found in neutral body posture positions, normal tilted seats set at these angles would not support a user and he or she would slide from the supporting surface. The chair of the present invention is specifically designed to support the user in the neutral body posture positions at the aforementioned body angular positions. The chair also provides a wide range of adjustability, not only to aid a user in mounting and obtaining an initial seated position in the chair before it is adjusted to the neutral body position angles, but also to accommodate individuals whose neutral body posture position would vary somewhat from the normal. The adjustability of the chair also permits the user to change positions while seated within the chair without having to dismount or loose supporting surfaces. This feature is particularly valuable when the chair is used in microsurgery.

In order that the chair of the present invention be used in the above-mentioned manner, it is provided with various structural features including a specifically designed molded seat structure to maintain the user in place in the neutral body posture position and it is provided with various adjustability features which permit the chair to function in the manner intended. The chair includes a molded seat structure having a seat pan, leg troughs, and a centrally located, elevated pommel which together form a saddle type configuration to support and maintain the user in a seated position when the seat is angled at the neutral body posture angle of approximately 127 degrees between the upper leg and trunk.

The seat further includes means for adjusting the seat vertically for height and means for tilting the seat between a 90 degree and 140 degree position using foot operated hydraulic controls. The range of adjustability permits a user to sit on the seat in a normal 90 degree position and enables the user to adjust the angle between 90 degrees and 140 degrees in order to accommodate various physiological differences between users permitting each individual the ability to adjust the chair to their specific neutral body position angles. The seat also includes a backrest which may be hydraulically operated by foot pedals and adjustable foot rests to accommodate the feet of the user in the most comfortable neutral body posture position. Preferably, the chair would include a suitable base platform on casters to provide mobility when it is needed.

FIG. 1 illustrates the neutral posture chair of the present invention with the seat in a position near its fully vertical tilt extension making an angle of approximately 127 degrees with the hydraulic vertical support column 14. The back support 16 is also shown in its fully extended horizontal tilt position. The figure also shows the seat jack piston 18 fully extended to its maximum vertical height. The chair includes a suitable base 20 which is shown as a rectangular plate but which can be any conventional base structure which will provide the stability and mobility necessary for this type of chair. The base includes casters 22 and may be provided with a caster lock 24 to stabilize the chair against movement during use. Footrests 26 are attached to the base 20 and are adjustable at an angle between 0 and 15 degrees from the horizontal which has proven to be the most comfortable for the user's foot during operative procedures. Details of the support structure and hydraulics as well as the various mechanical linkages are described in greater detail hereinbelow.

FIG. 2 illustrates the neutral body posture chair with the seat 12 in its fully lowered and horizontal position with the seat back 16 in its normal raised vertical position.

FIGS. 3, 4 and 5 illustrate the seat 12 in greater detail. FIG. 3 shows a prospective view, whereas FIG. 4 is a top plan view, and FIG. 5 is a sectional view taken along lines 5—5 of FIG. 4. The seat 12 forms a bowl 28 at the point where the pelvic and buttocks areas rest. The sides 30 of the seat are raised above the bottom of the bowl 28 to position a user in the seat without a great deal of lateral movement. Leg troughs 32 extend downwardly from the pelvic bowl 28 to form additional support under the upper leg structure of the user. The troughs 32 are generally semi-circular in shape as can be seen from the sectional view of FIG. 5 and are adapted to conform with the upper leg structure of the user. The seat is generally saddle shaped and includes a weight-bearing pommel 34 which projects upwardly below the bowl 28 and between the two leg troughs 32 and which is adapted to be straddled by the legs of the user. The forward end of the pommel 34 is in substantially the same plane as the forward end of the leg troughs 32. Because the pommel 34 is vertically raised from the bottom of the pelvic bowl 28, it provides support in the pubis bone area and the leg troughs support the upper leg of the user when the seat is tilted from a horizontal position to the neutral body posture angle of 127 degrees. Thus, when a surgeon or other user of the chair sits in the seat, the buttocks rest in the pelvic bowl 28 and the legs straddle the pommel 34 and are supported in the leg troughs 32. Preferably, the seat is covered with a cushion 36, as best seen in the sectional view of FIG. 4, and extends around the inside of the seat and covers the pelvic bowl 28 and leg troughs 32. The cushion also covers the portion of the pommel 34 which rests against the pubis bone to provide support in this area. The cushion 36 may be made of a suitable foam rubber structure although it is not limited thereto. Other materials providing a necessary softness and resiliency are equally applicable.

FIGS. 6, 7, 8, 9 and 10 show details of the seat pan and back support mechanisms. A seat mount 40 is formed by a vertical plate suitably attached to a support 42. The plate 40 is adapted to be screwed, bolted, or otherwise connected to the bottom of seat 12 which may be provided with a corresponding support plate (not shown) for stability and rigidity at the connection point. A hydraulic piston 44 of a seat tilt hydraulic cylinder 46 is attached by a threaded coupling member 48 to the bottom interior of the support 42. The cylinder and coupling preferably coact with a travel rod 50 mounted in a suitable guideway 52 so as to be freely moveable therewith by means of a pivot connection 54 as best seen from the sectional view of FIG. 8 and the exploded view of FIG. 10.

The seat support mechanism is mounted on a seat jack bracket 54 which is integrally connected with the seat jack piston 18 of the hydraulic vertical support column 14 which is adapted to raise and lower the entire seat assembly. The bracket 54 includes a stabilizer rod 60 which is telescopically moveable within an annular support 62 which in turn is mechanically connected to the column 14 by coupling member 64. This provides rigidity to the seat jack bracket 54 and prevents it from rotating in a horizontal plane. When the hydraulic vertical support column 14 is hydraulically operated, the seat jack piston 18 is moveable in a vertical direction which moves the seat bracket 54, rigidly attached thereto, upward or downward to adjust the height of the seat. The rod 60 moves within the coupling member 62 as the seat back at 54 is raised and lowered. A spring 66 is mounted in a housing 68 by means of a threaded rod 70 having a bumper 72 attached to the end thereof. The spring 66 bears against the rear wall of the housing 68. The bumper 72 bears against the support 42 so when the seat is tilted it is opposed by the tension of the spring 77 to provide resistance to the movement of the hydraulic piston 44. The entire seat mechanism is pivotably mounted on a threaded rod 74 which couples the support 42 to the spring housing 68 which in turn is coupled to the seat jack bracket 54.

The back support bracket 80 is pivotably mounted to the support 42 by a pivot pin 82. Sloted travelways 84 on the bracket 80 cooperates with corresponding travelway slots 86 on the support 42 allowing a threaded travel rod 88 to be moveable between the slots 84 and 86. The back support bracket 80 includes a vertical adjustment track 90 adapted to receive a vertical back support member 92. The back support 16 is suitably attached to the member 92 in a conventional manner preferably with a pivot connector 94 or the like. The vertical support 92 is connected to the back support bracket by a threaded screw 96.

The back support bracket 80 is moveable by means of a piston 98 moveable in a seat back tilt hydraulic cylinder 100. The hydraulic cylinder 100 in turn is rigidly mounted to an extension 102 of the seat support 42. The end of the piston 98 is mounted on the back of support bracket 80 by an annular coupling member 104 which is adapted to fit over a rod 106 which is moveable in a travelway slot 108.

FIGS. 11 and 12 illustrate the hydraulic and mechanical components for the vertical seat jack. The vertical support column 14, including the piston 18, is suitably connected to the seat jack bracket 54 as described hereinabove. A foot lever 110, adapted to be operated when the user is seated in the chair, is pivotably attached by a pivot pin 112 to the base member 20. A jack pressure rod 114, which controls the amount of hydraulic fluid into the cylinder 14 is moveable in a vertical direction against the bias of a spring 116 by means of a connector rod 118 mounted to the foot lever 110 by connector pins 120 and 122. Thus, by regulating the foot lever 110, the amount of hydraulic fluid in the cylinder 14 can be controlled to raise and lower the seat jack bracket 54 which in turn lowers or raises the entire seat mechanism in a vertical direction. A suitable on/off pressure switch 124 regulates the flow of hydraulic fluid from the source (not shown) to the hydraulic cylinder 14.

Figure 14:
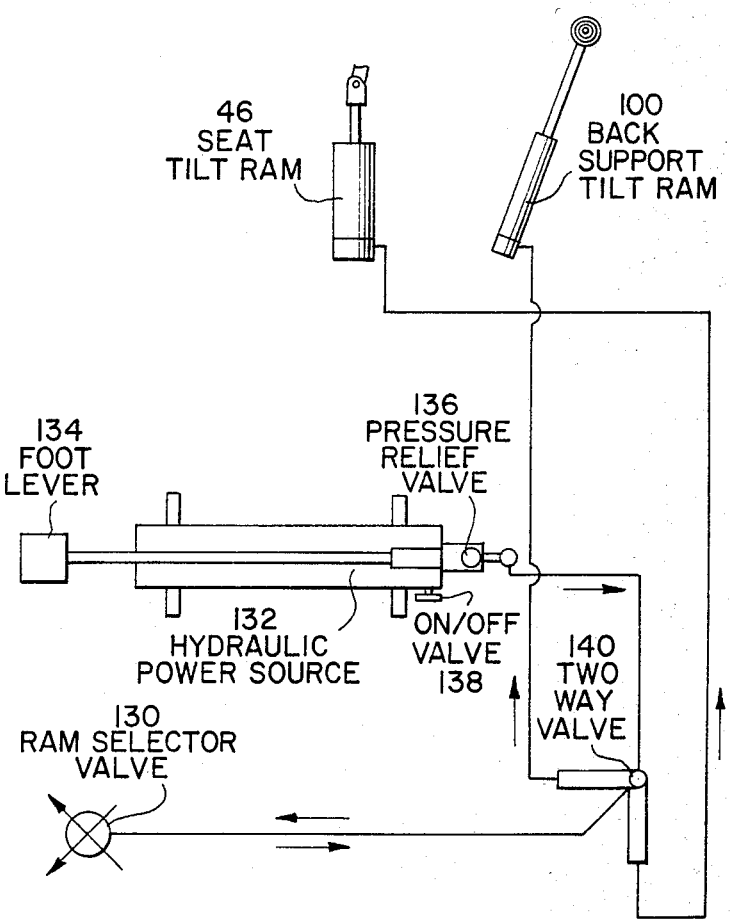
FIG. 14 is a schematic of a hydraulic circuit used with the invention of FIG. 1.

FIGS. 13 and 14 illustrate the hydraulic controls for the seat 12 and backrest 16. A remote, foot operated, selector valve 130 controls the flow of hydraulic fluid between the seat tilt cylinder 46 and the seat back tilt hydraulic cylinder 100. The hydraulic circuit includes a master power source cylinder 132, a foot operated control pedal 134, pressure relief valve 136, on/off valve 138, two-way valve 140, hydraulic line 142 to supply hydraulic fluid to seat tilt cylinder 46, and hydraulic line 144 to supply hydraulic fluid to seat back tilt cylinder 100.

As seen in the schematic of the hydraulic circuit, the position of the selector valve 130 controls the fluid flow through the two-way valve 140, which in turn regulates the flow of fluid to either cylinder 46 or 100.

FIGS. 15 and 16 show the on/off pressure controls for the seat vertical control cylinder 14. A lever 150 is rotatably mounted on a support post 152 and is operably connected to a cable 156, the other end of which is connected to an operating mechanism 158 including a bracket 160 which is operably secured to a control lever for the pressure on/off valve 138. Movement of the lever 150 regulates the position of the operating mechanism 158 and controls the position of the pressure on/off valve 138. It will be appreciated that this arrangement is exemplary only and that other hydraulic control means may be used. Also it will be appreciated that similar control means may be used for the remainder of the hydraulic circuits.

FIG. 17 illustrates the foot rests 26 which are pivotably mounted on the base 20 by means of a suitable pin 170 or the like. The foot rests are angularly adjustable between zero and 15 degrees by an adjusting mechanism shown as a rod 172 moveable in a slot 174. This arrangement is shown by way of example and other suitable adjusting means may be used.

The operation of the chair may be described briefly as follows:

The hydraulic systems are turned on using the on/off pressure controls shown in FIGS. 15 and 16 by movement of the operating lever 150 to the on position. The footrests are adjusted at an angle which is most comfortable for the user.

With the user seated in the seat 12, the vertical cylinder 18 is operated by means of the foot lever 110 to raise the entire seat assembly to the height necessary for the user to be comfortable in a work position. Next, the foot operated control lever 130 is selected to enable the user to position the seatback or to adjust the seat tilt. Assuming both operations are necessary, and that the control lever 130 is in a position which enables hydraulic fluid to be fed to the seat tilt cylinder 46, operation of the foot pedal 134 will pump fluid into the cylinder 46 thereby raising piston 44 in a vertical direction. The seat support 42, which is operably connected to the piston 44 through the coupling arrangement described hereinabove, pivots about the rod 74 and is raised in the vertical direction. This in turn tilts the seat which is mounted on the plate 40 until it reaches the most comfortable neutral body posture position, which as described hereinabove is approximately 127 degrees. The user then sits in the chair at this angle and is supported by the configuration of the seat including the seat bowl 28, the leg troughs 32, and the pommel 34.

In this seated position, if it becomes necessary to adjust the backrest 16, the foot operated selector valve 130 is moved to its opposite position which allows hydraulic fluid to flow in the circuit to the back support tilt cylinder 100. Again, operating the foot lever, fluid is pumped into the cylinder 100 which causes piston 98 to move the seat back support 80 tilting it as it rotates about the linkage shown in detail hereinabove.

With this arrangement, the height, the seat back and the seat tilt are readily controlled without necessitating the user in the seat to use his hands to operate the controls. This is particularly useful during operations when surgeons require the use of their hands at all times. The foot controls enable the position of the seat to be comfortably moved while maintaining the attention necessary for operations.

It will be appreciated that the above description relates to a preferred embodiment of the invention. However, various other controls other than the hydraulic controls described above may be used without departing from the spirit and scope of the invention which is to provide a chair to support a user in a neutral body posture position such as experienced during weightlessness. For example, mechanical, electromechanical, electrical and various other combinations are among the controls which could be used with the present invention. Hand controls may be used in place of foot controls making the chair suitable for handicapped persons who normally use a wheel chair.

Similarly, seat structures other than those shown may be used to support the user when the seat is in the tilted body posture position angle. Therefore, it will be understood that the above description is illustrative of the principles of the present invention and that numerous modifications and variations thereof may be made as evidence to one of ordinary skill in the art in keeping within the spirit and scope of the invention as defined in the following claims.

I claim:

1. A chair adapted to support a user in a neutral body posture position; said position defined as the position the body assumes during weightlessness wherein the torso of the body and upper legs form an angle with respect to each other within a range of 100–140 degrees, and the upper legs and the lower legs form a second angle with respect to each other within the range of 100–140 degrees; comprising: a base; a vertical support means; a seat attached to said vertical support means; said seat having a back portion and a front portion; said front portion being downwardly inclined from said back portion at a neutral body posture position angle between 100–140 degrees with respect to the vertical axis of said chair; said back portion of said seat forming a contoured bowl having lower supporting surfaces and raised sides adapted for reception and support of the buttocks of a user; said front portion of said seat forming semi-cylindrical leg troughs extending forwardly of said contoured bowl, said troughs having lower supporting surfaces and raised sides conforming to and being adapted for reception and support of the upper legs of a user; and an elevated weight-bearing pommel positioned between said leg troughs and raised above said lower supporting surfaces of said contoured bowls; the forward end of said pommel and the forward end of said leg troughs being in substantially the same plane; said weight-bearing pommel supporting the weight of the user at the pubis bone maintaining the user at an inclined neutral body position angle within said seat.

2. The chair of claim 1 further including an adjustable back rest disposed in a vertical plane with respect to the base of said chair and at an angle of 100–140 degrees with respect to the inclined axis of said seat.

3. The chair of claim 1 wherein the supporting means supports the user at an angle of approximately 127 degrees.

4. The chair of claim 1 further including means for adjusting the height of said seat with respect to said base.

5. The chair of claim 1 further including means for adjusting the position of said seat to vary said neutral body position angle.

6. The chair of claim 1 further including second supporting means for supporting the feet and lower legs of a user at an angle of approximately 130 degrees between the lower and upper legs.

7. The chair of claim 6 wherein said second supporting means are footrests.

8. The chair of claim 7 wherein said footrests are adjustable between an angle of 0 and 15 degrees with respect to said base.

9. The chair of claim 4 wherein said adjusting means includes a vertical jack and a foot operated control means for adjusting the height of said seat.

10. The chair of claim 9 wherein said vertical jack is formed of a hydraulic piston and said foot operated control means is a hydraulic control lever adapted to regulate hydraulic fluid flow in said hydraulic piston.

11. The chair of claim 5 wherein said seat includes a pivotable attachment between said seat and said base member and said adjusting means is a moveable member adapted to engage the lower surface of said seat whereby movement of said moveable member causes said seat to pivot about said pivotable attachment to adjust the angle of the seat.

12. The chair of claim 11 wherein said moveable member is a hydraulic piston and said adjusting means further includes a foot operated hydraulic control means for regulating hydraulic fluid flow to operate said hydraulic piston.

13. The chair of claim 2, further including a pivot connection for attaching said adjustable back rest to said seat and a moveable adjustment member for moving said back rest about said pivot connection.

14. The chair of claim 13 wherein said adjustment member is a hydraulic piston and further including a foot operated hydraulic control means for regulating hydraulic flow to operate said hydraulic piston.

* * * * *